(12) United States Patent
Yaginuma et al.

(10) Patent No.: US 10,223,558 B2
(45) Date of Patent: Mar. 5, 2019

(54) EXTERNAL OPERATION CONTROL DEVICE, ARTICLE POSITION ACQUIRING SYSTEM, AND ARTICLE POSITION AQUIRING METHOD

(71) Applicant: TOSHIBA TEC KABUSHIKI KAISHA, Tokyo (JP)

(72) Inventors: Jun Yaginuma, Izunokuni Shizuoka (JP); Sadatoshi Oishi, Fuji Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/642,203

(22) Filed: Jul. 5, 2017

(65) Prior Publication Data

US 2018/0053023 A1 Feb. 22, 2018

(30) Foreign Application Priority Data

Aug. 18, 2016 (JP) .................................. 2016-160783

(51) Int. Cl.
| | |
|---|---|
| *G06K 7/00* | (2006.01) |
| *G06K 7/10* | (2006.01) |
| *B01L 3/00* | (2006.01) |
| *G06K 19/07* | (2006.01) |

(52) U.S. Cl.
CPC ........ *G06K 7/10366* (2013.01); *B01L 3/5453* (2013.01); *G06K 7/0008* (2013.01); *G06K 7/10118* (2013.01); *G06K 7/10158* (2013.01); *G06K 19/0716* (2013.01)

(58) Field of Classification Search
USPC ........................................................ 235/451
See application file for complete search history.

(56) References Cited

U.S. PATENT DOCUMENTS

| | | |
|---|---|---|
| 2014/0266628 A1 | 9/2014 | Kawasaki |
| 2016/0188918 A1* | 6/2016 | Nikitin ............... G06K 7/10128 340/10.51 |

FOREIGN PATENT DOCUMENTS

| | | |
|---|---|---|
| JP | 2004-271299 A | 9/2004 |
| JP | 2012-231357 A | 11/2012 |
| WO | 2013050849 A1 | 4/2013 |

OTHER PUBLICATIONS

European Search Report dated Jan. 17, 2018, mailed in counterpart European Application No. 17185731.1, 8 pages.

* cited by examiner

*Primary Examiner* — Rafferty Kelly
(74) *Attorney, Agent, or Firm* — Kim & Stewart LLP

(57) ABSTRACT

A control device for wireless tags which are respectively attached to a plurality of articles supported respectively on a plurality of support portions and respectively store identification numbers of the articles, includes positioning portions that are respectively provided corresponding to the plurality of support portions, and input devices that are positioned respectively in the positioning portions. The input devices are individually controllable and each is configured to switch a flag status of one of the wireless tags.

13 Claims, 17 Drawing Sheets

FIG. 10

| ID | FLAG STATUS |
|---|---|
| AAAABBBBCCCC | OFF |
| AABBCCDDEEFF | ON |
| BBFF55449455 | OFF |
| CCAABBBBCCAA | OFF |

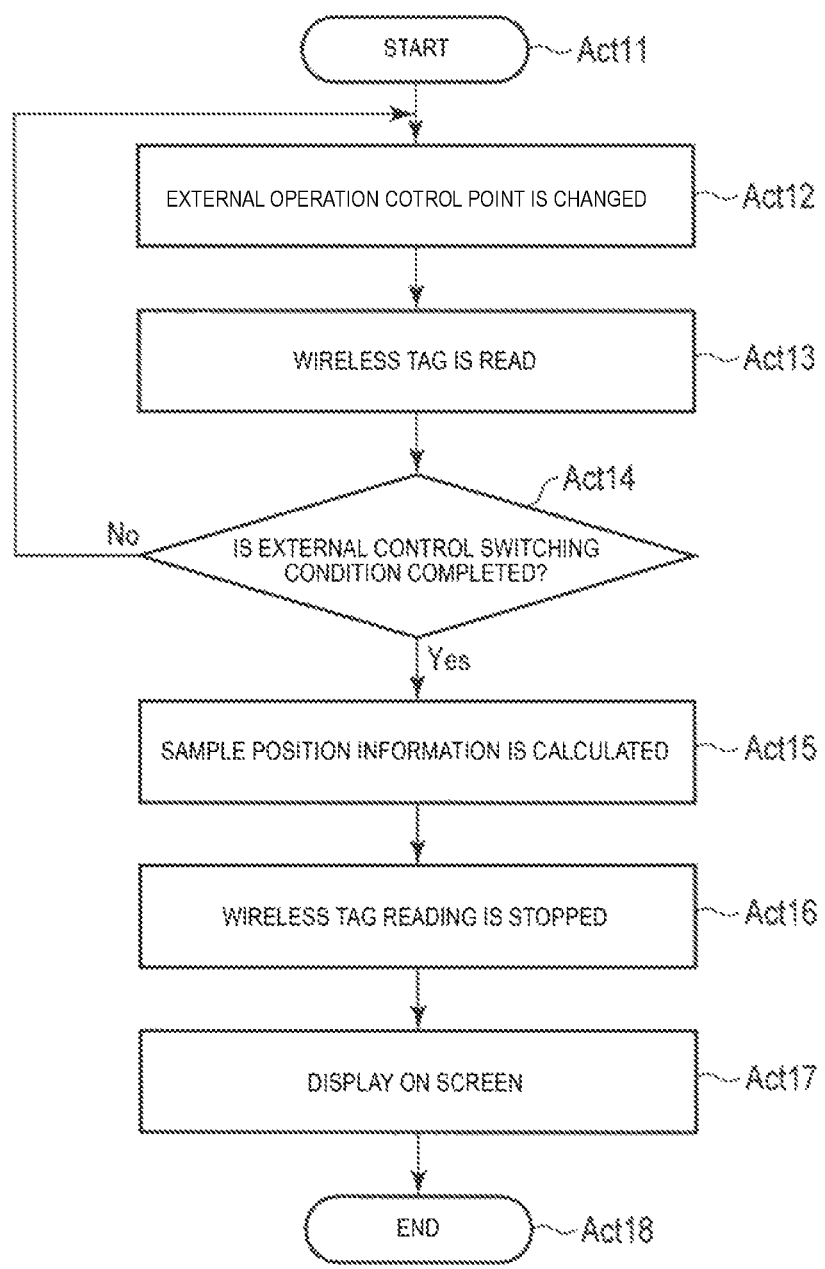

FIG. 12A m=1

| ID | FLAG STATUS |
|---|---|
| A000025439B | OFF |
| A000000009832 | ON |
| B000000000684 | OFF |
| A000001206123 | OFF |
| ... | |
| A000045897G | ON |
| B00000000211 | OFF |
| B000000004885 | OFF |

FIG. 12B m=3

| ID | FLAG STATUS |
|---|---|
| B000000000684 | OFF |
| B000000004885 | ON |
| BBFF55449453 | ON |
| CCAABBBBCCAA | ON |
| ... | |
| A000001206123 | OFF |
| AABBCCDDEEFF | OFF |
| AAAABBBBCCCC | OFF |

FIG. 12C m=5

| ID | FLAG STATUS |
|---|---|
| AAAABBBBCCCC | ON |
| A0000458876 | OFF |
| BBFF55449453 | OFF |
| CCAABBBBCCAA | OFF |
| ... | |
| AABBCCDDEEFF | ON |
| B000000000684 | OFF |
| A000025439B | OFF |

FIG. 12D r=1

| ID | FLAG STATUS |
|---|---|
| A000009832 | ON |
| AABBCCDDEEFF | OFF |
| BBFF55449455 | OFF |
| CCAABBBBCCAA | OFF |
| ... | |
| B000000884 | OFF |
| B000004885 | OFF |
| A0000254388 | ON |

FIG. 12E r=2

| ID | FLAG STATUS |
|---|---|
| B000000211 | ON |
| AABBCCDDEEFF | ON |
| BBFF55449455 | OFF |
| A000009832 | OFF |
| ... | |
| CCAABBBBCCAA | ON |
| AAAABBBBCCCC | OFF |
| A0000458870 | OFF |

FIG. 12F r=3

| ID | FLAG STATUS |
|---|---|
| A000009832 | OFF |
| B000004885 | ON |
| BBFF55449455 | OFF |
| B000000211 | OFF |
| ... | |
| AABBCCDDEEFF | OFF |
| B000000884 | OFF |
| CCAABBBCCAA | OFF |

EXTERNAL OPERATION CONTROL DEVICE, ARTICLE POSITION ACQUIRING SYSTEM, AND ARTICLE POSITION AQUIRING METHOD

CROSS-REFERENCE TO RELATED APPLICATION

This application is based upon and claims the benefit of priority from Japanese Patent Application No. 2016-160783, filed Aug. 18, 2016, the entire contents of which are incorporated herein by reference.

FIELD

Embodiments described herein relate generally to an article position acquiring system capable of collectively reading wireless tags attached to articles and acquiring positions of the articles, an external operation control device used in the article position acquiring system, and an article position acquiring method.

BACKGROUND

When performing a blood test on a patient in a hospital or the like, a plurality of sample containers containing blood are collected in a sample rack after collecting blood in a blood collecting room. Thereafter, the sample containers are brought to an analysis room and various analyses are performed in the analysis room. In this case, in order to link the patient from which the blood is sampled and the sample, a barcode is attached to the sample container. When moving the sample rack between rooms, the samples are checked by reading the barcodes and measures to prevent loss are taken.

In recent years, instead of the barcode, a method of attaching a wireless tag such as an RFID tag to the sample container and managing the sample container using a wireless tag reader has been adopted. According to the method using the wireless tag, it is possible to wirelessly and collectively read the wireless tags attached to several to several tens of sample containers. Therefore, it is possible to check the sample containers in a short period time. However, there are cases in which the wireless tag is actually overlooked, and in that case, it is necessary to read again the wireless tags attached to each sample container one by one.

Such a problem can be solved if it is possible to acquire a position of the wireless tag that cannot be read in the sample rack by some method. That is, even if the wireless tag is overlooked, it can be settled by re-reading only the wireless tag attached to the sample container at a particular position, so that the operation can be simplified. Therefore, there is a demand for a sample rack device capable of acquiring the reading status of the wireless tag and the position of the sample container by linking therebetween. In the device, a wireless tag reader is provided in each of portions of the sample rack, which contain the sample containers, and information read from the wireless tag by the wireless tag reader is linked with position information of the wireless tag reader which read the wireless tag so as to acquire the position information of the sample container. With such a device, even if the wireless tag reader cannot read the information from any of the wireless tags due to some cause despite the presence of the sample container, only the wireless tag reader needs to perform a reading operation again, and it is possible to greatly simplify the operation.

However, the sample rack device which is described above requires the same number of wireless tag readers as the number of samples to be loaded, the device becomes expensive, and the weight thereof increases. Therefore, it is not appropriate for use as a sample rack for transportation. Also, in order to reduce the weight, it is conceivable to make the sample rack for reading different from the sample rack for transportation, but in such a case, an operation of transferring the sample containers between the sample rack for reading and the sample rack for transportation occurs before and after reading, thereby increasing an operator's burden.

For this reason, there is a demand for a device which is inexpensive, can identify the sample container and the position of the sample container while using a common sample rack.

DESCRIPTION OF THE DRAWINGS

FIG. 10 is an explanatory view illustrating an example of a reading result of the wireless tag in the embodiment.

FIG. 11 depicts a flowchart of another example of the operation of the article position acquiring system in the embodiment.

FIGS. 12A to 12F are explanatory views illustrating an example of the reading result of the wireless tag in the embodiment.

DETAILED DESCRIPTION

Embodiments provide an article position acquiring system capable of collectively reading wireless tags attached to articles and acquiring positions of the articles, an external operation control device used in the article position acquiring system, and an article position acquiring method.

In general, according to an embodiment, there is provided a control device for wireless tags which are respectively attached to a plurality of articles supported respectively on a plurality of support portions and respectively store identification numbers of the articles. The control device includes positioning portions that are respectively provided corresponding to the plurality of support portions, and input devices that are positioned respectively in the positioning portions. The input devices are individually controllable and each is configured to switch a flag status of one of the wireless tags.

In one embodiment, the input device is an external operation unit 120 described below. In other embodiments, the input device may be an external operation unit 120A or 120B described below.

Hereinafter, embodiments will be described with reference to the drawings.

Figure 1:
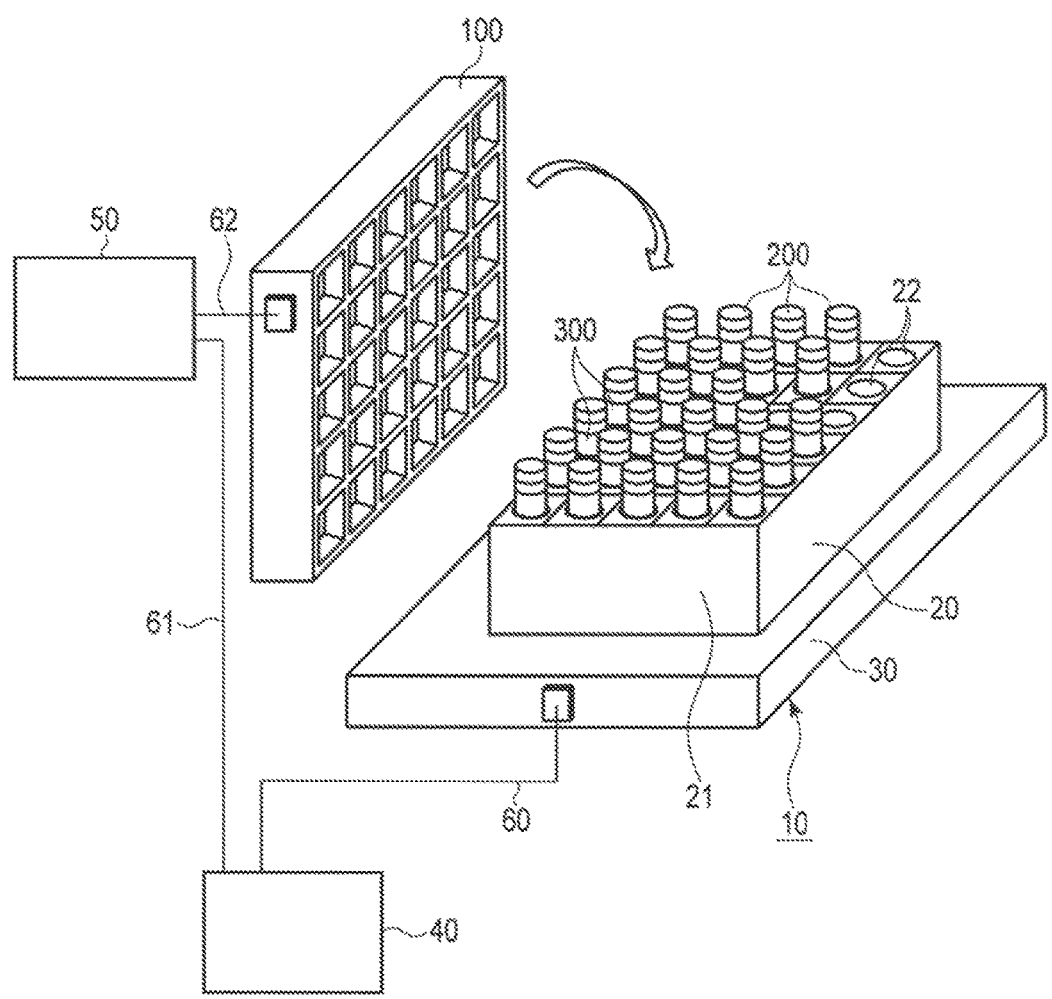
FIG. 1 is an explanatory view of an article position acquiring system according to an embodiment.

FIG. 1 is an explanatory view illustrating a configuration of an article position acquiring system 10 incorporating an external operation control device 100 according to an embodiment. The article position acquiring system 10 is disposed in, for example, a sample analysis room of a hospital or the like and is used for the purpose of managing position information of a sample or the like. Reference numeral 200 in FIG. 1 denotes a sample container, reference numeral 300 denotes a wireless tag with an external input function, and the wireless tag 300 attaches to each sample container 200. Position information in the embodiment means, for example, at least one of direct information that is a position located in m rows and n columns and indirect information having a relationship with a known position (m rows and n columns).

The article position acquiring system 10 includes a sample rack 20 that can support a plurality of sample containers 200, an antenna device 30 that is disposed at a lower portion of the sample rack 20 and reads a signal from the wireless tag 300, a wireless communication device 40 that is connected to the antenna device 30, an information processing terminal 50 that controls a reading operation using the antenna device 30 or a displaying operation which will be described later, and processes the signal received by the wireless communication device 40, and the external operation control device 100 that is detachably attached to an upper portion of the sample rack 20.

The antenna device 30 and the wireless communication device 40 are connected by a cable 60, the wireless communication device 40 and the information processing terminal 50 are connected by a cable 61, and the external operation control device 100 and the information processing terminal 50 are connected by a cable 62. As the cables 60, 61, and 62, for example, a LAN cable, a USB cable, a coaxial cable, or the like may be used.

The sample rack 20 is provided with a rectangular box body 21 and thirty support portions 22 that are provided in 6 rows and 5 columns within the box body 21 and support lower portions of the sample containers 200. The support portion 22 is formed to have such a size that the wireless tag 300 attached to the sample container 200 is exposed to the outside of the sample rack 20 in a case where the support portion 22 supports the sample container 200.

Figure 2:
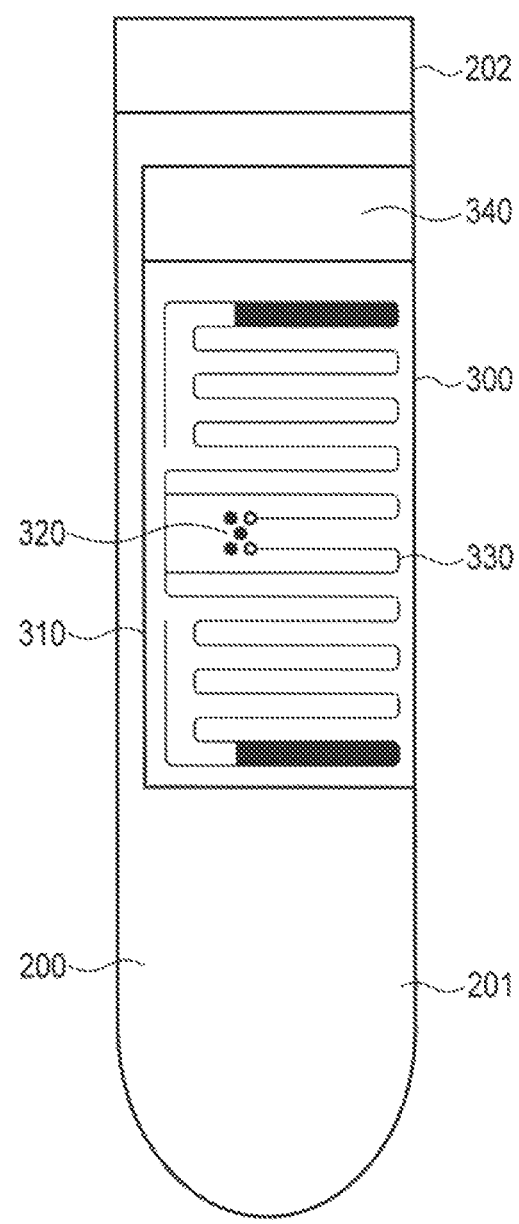
FIG. 2 is a front view illustrating a sample container to which a wireless tag with an external operation function is attached in the embodiment.

As illustrated in FIG. 2, the sample container 200 includes a container body 201 that contains a sample such as blood and a cap 202 that closes an opening portion of the container body 201. The wireless tag 300 attaches to, for example, upper portion of an outer surface of the container body 201.

The wireless tag 300 has a unique identification number and a memory area in which information can be recorded and rewritten such that reading of the identification number, or writing and reading of arbitrary information in a non-contact manner with wireless can be performed.

Figure 3:
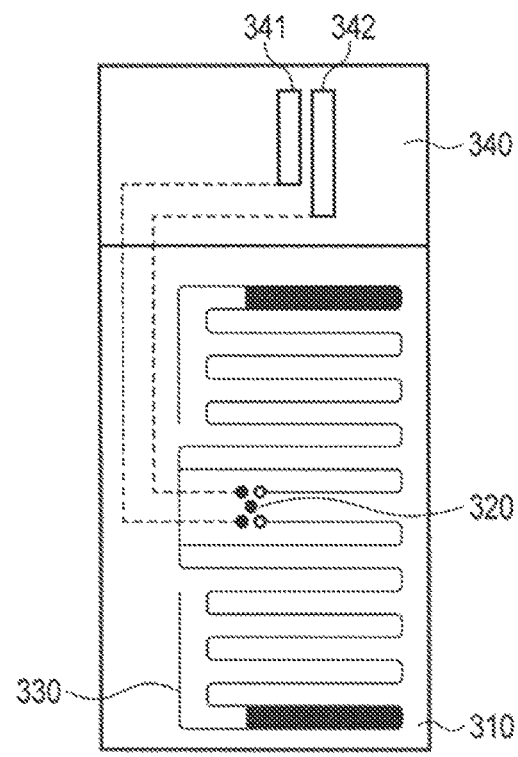
FIG. 3 is a front view illustrating the wireless tag with the external operation function in the embodiment.

As illustrated in FIG. 3, the wireless tag 300 includes a base portion 310 attached to the container body 201, an IC chip 320 provided on the base portion 310, an antenna 330 connected to the IC chip 320, and an input unit 340 connected to the IC chip 320. The input unit 340 includes a pair of external input terminals 341 and 342. The external input terminals 341 and 342 are disposed apart from each other in a circumferential direction with respect to the container body 201. In addition, the external input terminals 341 and 342 may be disposed apart from each other in an axial direction or in some other direction depending on the configuration of the external operation control device 100.

The IC chip 320 maintains a flag that indicates whether or not the external input terminals 341 and 342 are electrically connected. While the external input terminals 341 and 342 are electrically connected, the flag is set (e.g., set to 1) to indicate that the external input terminals 341 and 342 are electrically connected. On the other hand, while the external input terminals 341 and 342 are not electrically connected, the flag is not set (e.g., cleared to 0) and does not indicate that the external input terminals 341 and 342 are electrically connected. When the wireless communication device 40 transmits radio waves to the wireless tag 300 while the wireless tag 30 is in a response range of the wireless communication device 40, the wireless tag 300 responds with its identification number and with its flag status indicating whether or not the external input terminals 341 and 342 are electrically connected.

Figure 4:
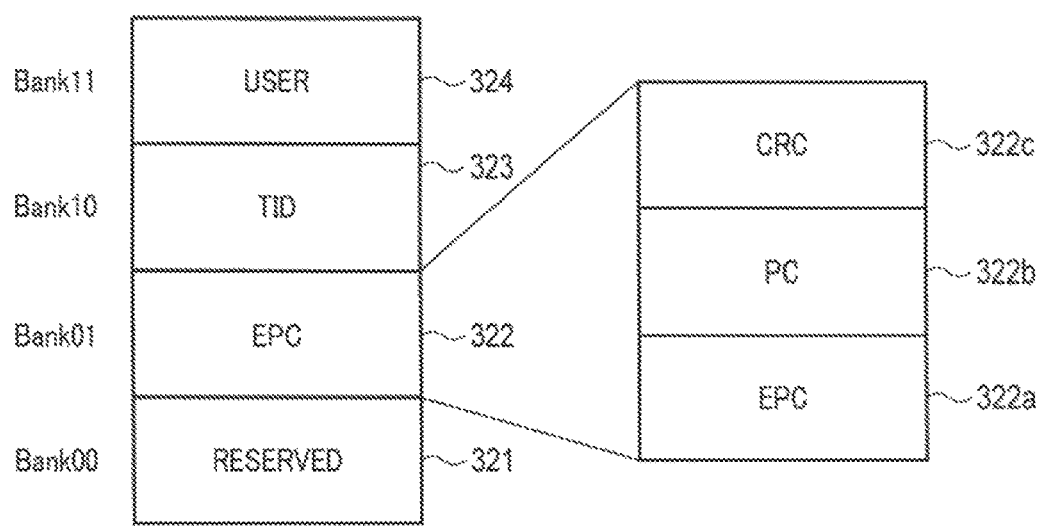
FIG. 4 is an explanatory view illustrating a memory structure of the wireless tag with the external operation function in the embodiment.

FIG. 4 illustrates a memory structure of the IC chip 320. Here, explanation will be given with reference to UHF band RFID conforming EPCglobal Class1 generation2. The memory is composed of four memory banks. In FIG. 4, reference numeral 321 denotes Bank00 RESERVED memory, reference numeral 322 denotes Bank01 EPC memory, reference numeral 323 denotes Bank10 TID-memory, and reference numeral 324 denotes Bank11 USER-memory. Further, the Bank01 EPC memory 322 is provided with an EPC region 322a, a PC region 322b, and a CRC region 322c. The identification number is stored in the Bank01 EPC memory 322. The flag status, described above, is stored in the Bank01 EPC memory 322 or stored in the Bank11 USER memory 324.

Figure 5:
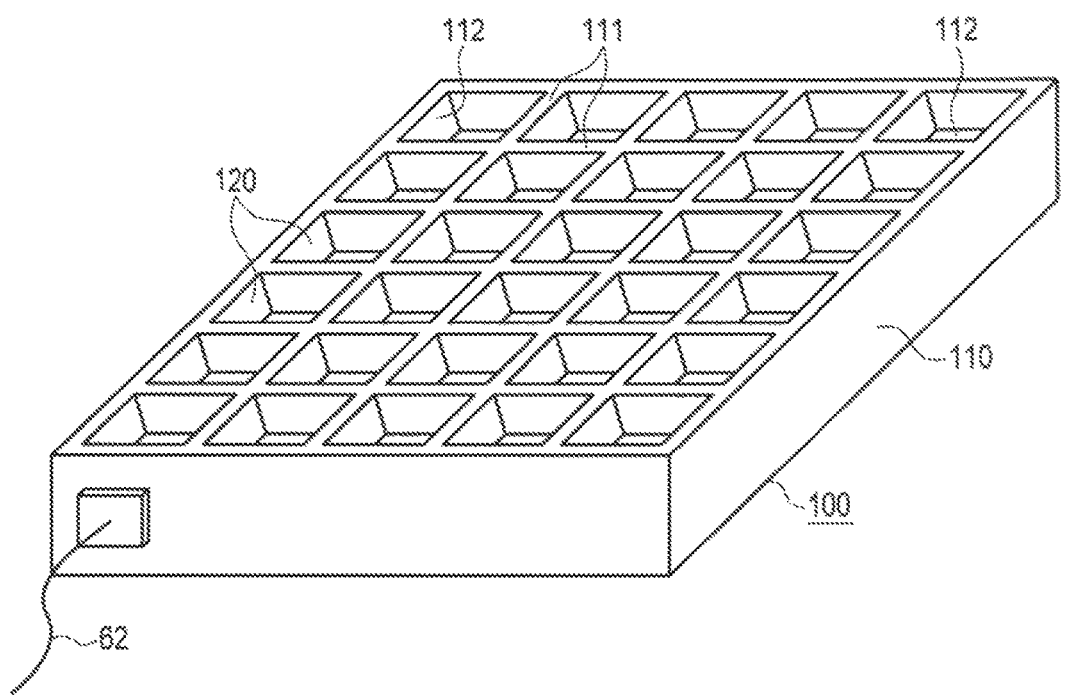
FIG. 5 is a perspective view illustrating an external operation control device in the embodiment.

FIG. 5 is a perspective view illustrating the external operation control device 100. The external operation control device 100 can be detachably attached to the sample rack 20. The external operation control device 100 includes a rectangular frame body 110 and partition walls 111 that divide vertically and horizontally in the frame body 110. The partition walls 111 divide the inside of the frame body 110 into 6 rows and 5 columns so that recessed portions 112 are formed respectively corresponding to the support portions 22 of the sample rack 20 described above. That is, thirty recessed portions 112, which cover upper portions of the sample containers 200 contained in the support portions 22 of the sample rack 20, is formed in the external operation control device 100. Each recessed portion 112 is positioned adjacent to the sample container 200 supported by the sample rack 20 in a case where the external operation control device 100 is attached to the sample rack 20. An external operation unit 120 is provided within each recessed portion 112.

Figure 6:
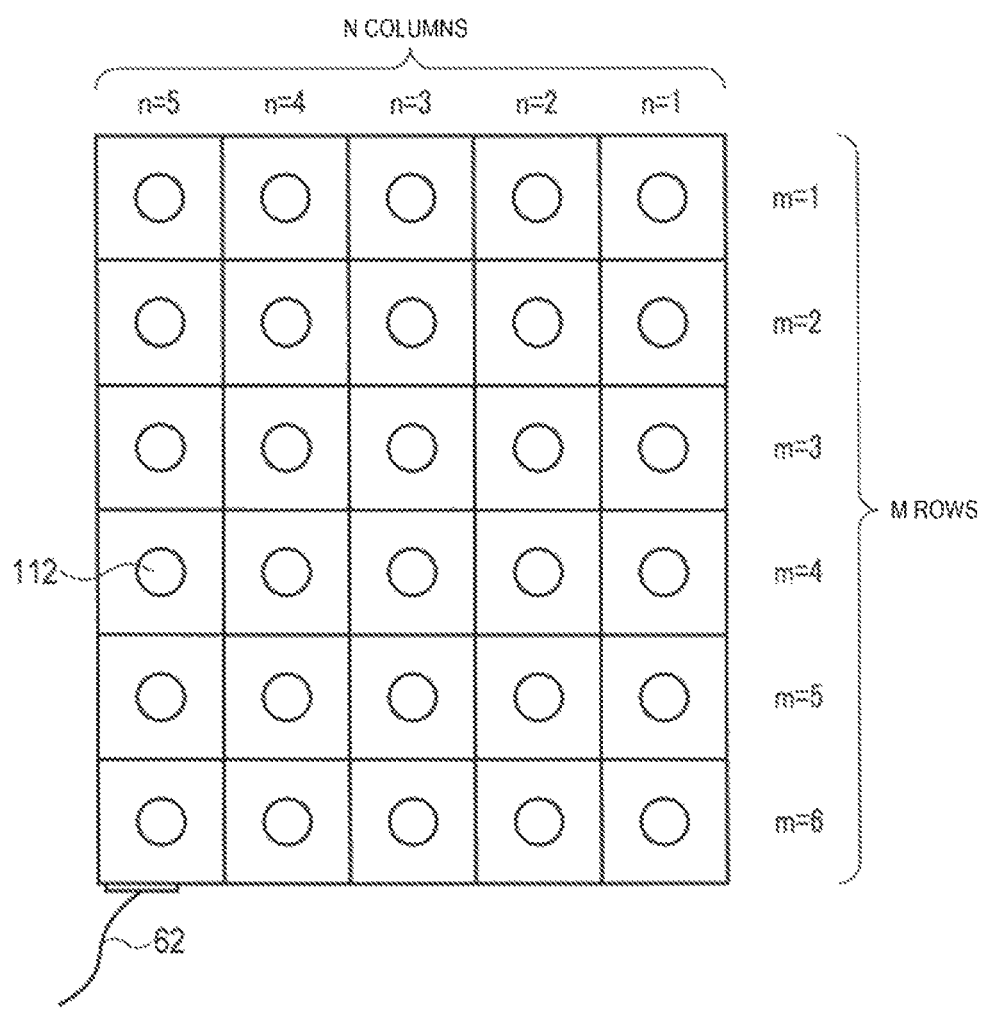
FIG. 6 is an explanatory view illustrating each partition position of the external operation control device in the embodiment.

FIG. 6 is an explanatory view illustrating each partition position of the external operation control device 100. For each recessed portion 112, position information is set at a point (m, n) in M rows and N columns.

Figure 7:
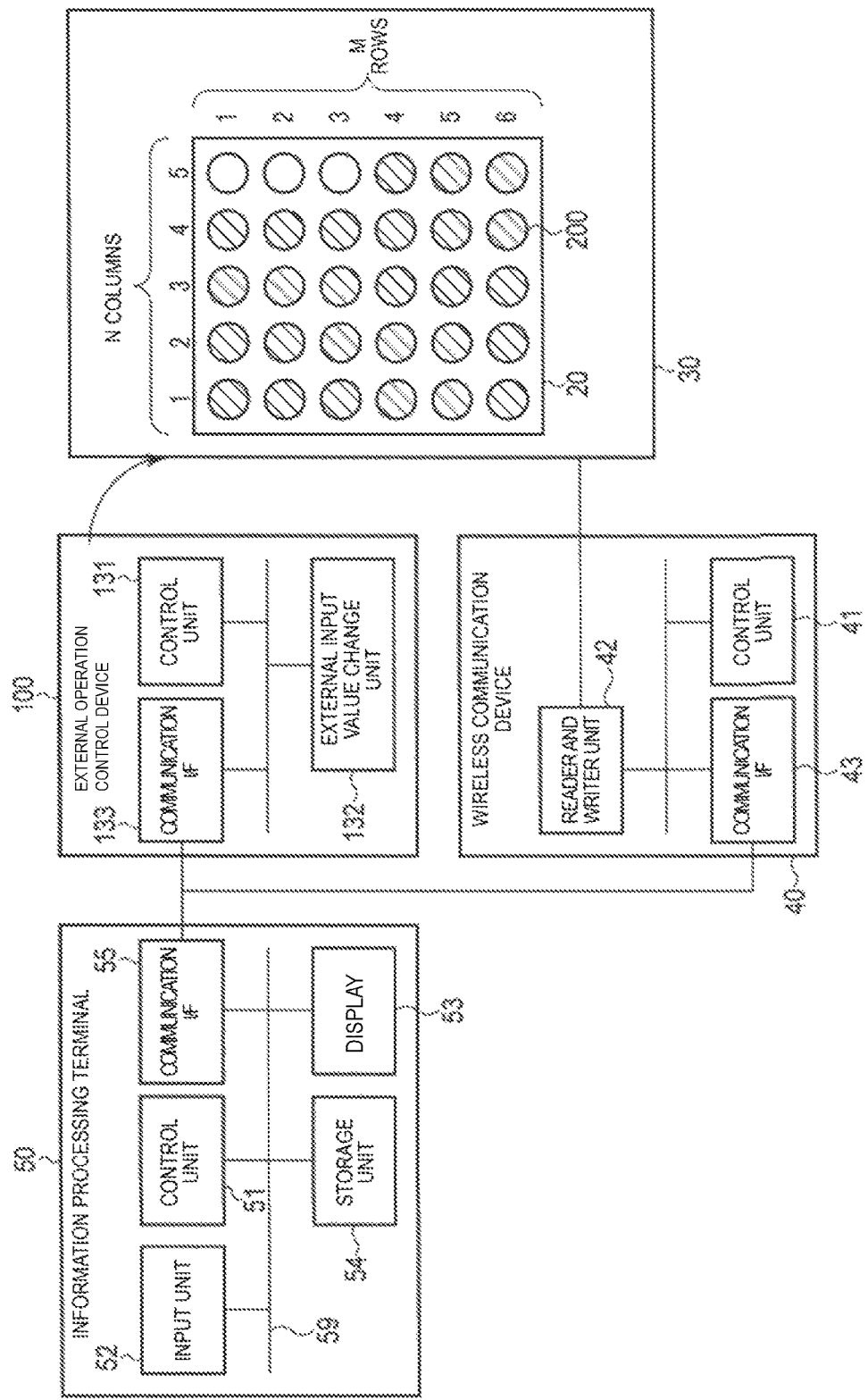
FIG. 7 is a block diagram of an article position acquiring system in the embodiment.

FIG. 7 illustrates a control block diagram of the wireless communication device 40, the information processing terminal 50, and the external operation control device 100 of the article position acquiring system 10. As illustrated in FIG. 7, the wireless communication device 40 includes a control unit 41 of a computer configuration including a Central Processing Unit (CPU), a Read Only Memory (ROM), a Random Access Memory (RAM), and the like. The ROM stores various programs to be executed by the CPU and various data. The RAM temporarily stores data and programs when the CPU executes various programs.

The control unit 41 connects to a reader and writer unit 42, a communication interface 43, and the like via various input and output circuits (not illustrated).

The reader and writer unit 42 communicates with the wireless tag 300 attached to the sample container 200 and transmits and receives data through the antenna device 30 under instructions from the control unit 41. For example, an unmodulated carrier wave is amplified and radiated as a radio wave from the antenna device 30, and in the wireless tag 300 in a response range of the radiated radio wave, tag information of the wireless tag 300 such as an identification code placed on a reflected wave is received by the antenna device 30, the received tag information is demodulated from the carrier wave, and a read cycle, in which the demodulated tag information is transmitted to the control unit 51, is performed.

The information processing terminal 50 includes a control unit 51 of a computer configuration including a CPU, a ROM, a RAM, and the like. The control unit 51 executes data processing relating to loading and unloading of the sample container 200 based on information read from the wireless tag 300 attached to the sample container 200 via the antenna device 30. The control unit 51 connects to an input unit 52, a display 53, a storage unit 54, and a communication interface 55 via a bus line 59. The input unit 52 receives an operation input by a user. The storage unit 54 is a storage device including a nonvolatile storage medium such as a Hard Disk Drive (HDD) or a Solid State Drive (SSD). The storage unit 54 stores various programs and various data relating to the operations of the wireless communication device 40, the information processing terminal 50, and the external operation control device 100. The data stored in the storage unit 54 includes, for example, a sample master registering a sample code for identifying a sample and a patient in association with each other. The communication interface 55 is an interface for transmitting and receiving various data to and from the external operation control device 100.

The external operation control device 100 includes a control unit 131 of a computer configuration including a CPU, a ROM, a RAM, and the like. The control unit 131 includes an external input value change unit 132 for operating the external operation unit 120 based on a command from the information processing terminal 50 and a communication interface 133 that is an interface for transmitting and receiving various data to and from the information processing terminal 50.

Figure 8:
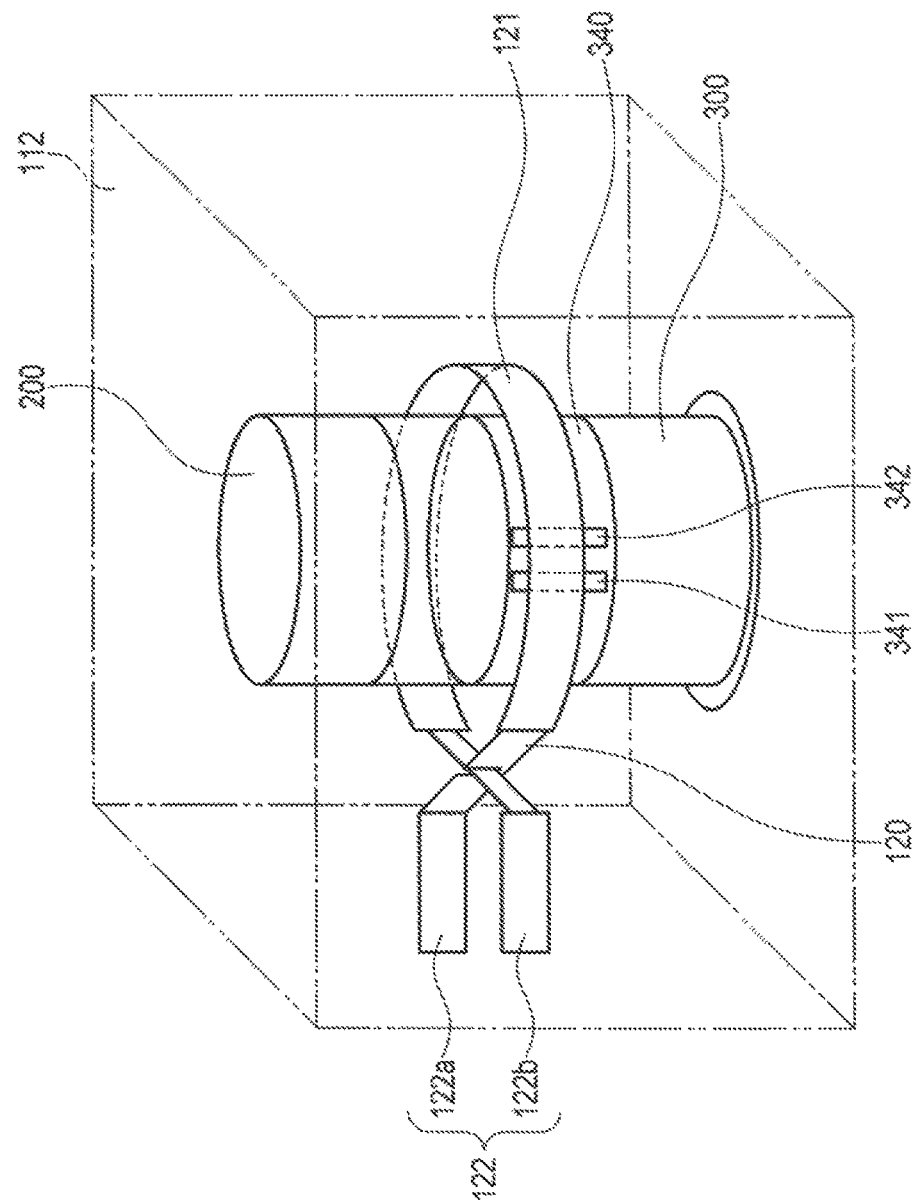
FIG. 8 is a perspective view illustrating an external operation unit in the embodiment.

FIG. 8 illustrates the external operation unit 120. Here, the external operation control device 100 is positioned at the upper portion of the sample rack 20, and the recessed portion 112 covers the upper portion of the sample container 200.

The external operation unit 120 has a metallic annular portion 121 which surrounds the sample container 200 along the circumferential direction at the position of the input unit 340. Apart of the annular portion 121 in the circumferential direction is cut out, and each end portion is provided on an inner wall surface side of the recessed portion 112, and is connected to an operating portion 122 which changes a diameter of the annular portion 121. The operating portion 122 has a fixed end 122a and a moving end 122b. As the moving end 122b moves in the horizontal direction, the annular portion 121 is reduced in diameter and abuts against the pair of external input terminals 341 and 342. In this case, the pair of external input terminals 341 and 342 conduct through the annular portion 121 and are electrically connected to each other. The annular portion 121 expands in diameter so that the external input terminals 341 and 342 are no longer electrically connected, by returning a moving end 122b to an original position. That is, in the external operation unit 120, it is possible to change the external input terminals 341 and 342 between a first state in which the external input terminals 341 and 342 are electrically connected and a second state in which the external input terminals 341 and 342 are not electrically connected.

Figure 9:
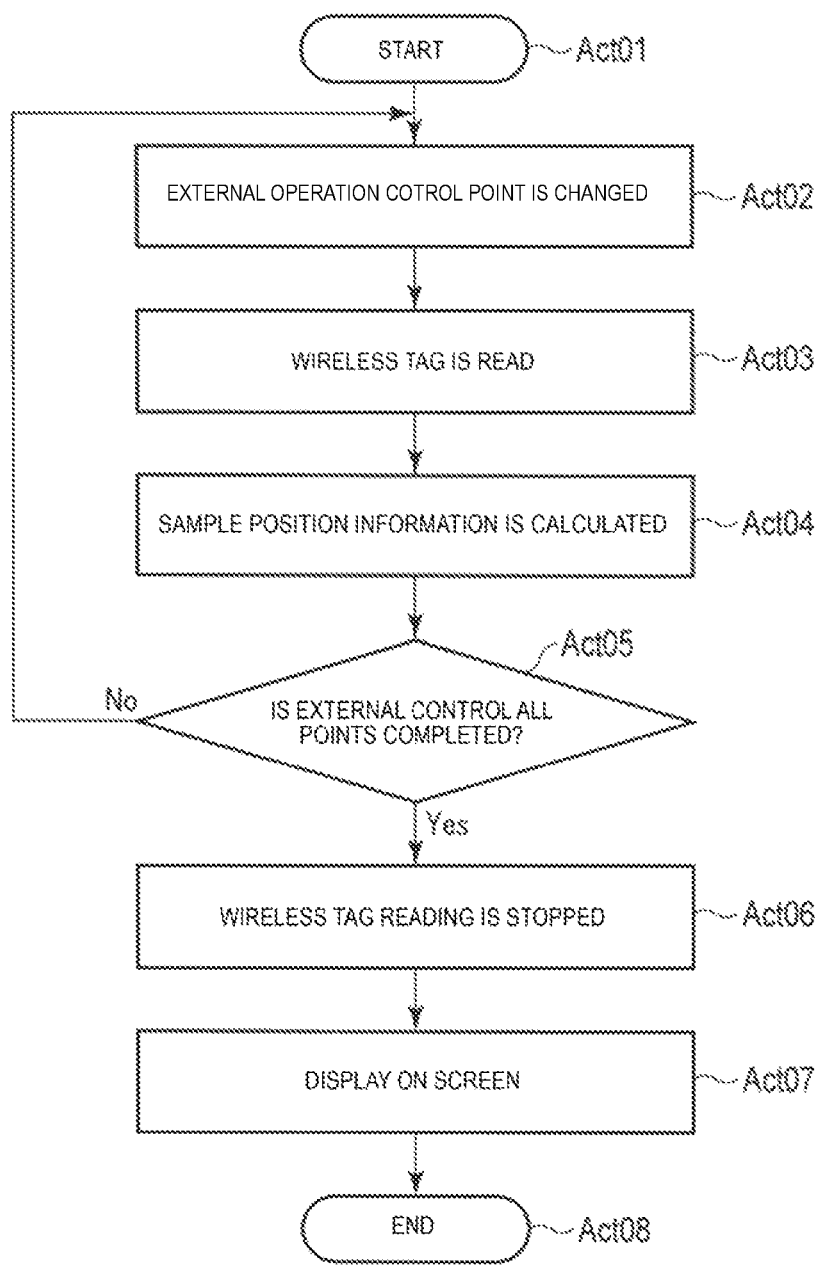
FIG. 9 depicts a flowchart of an example of an operation of the article position acquiring system in the embodiment.

The article position acquiring system 10 configured as described above operates as follows to identify the position of the sample container 200. FIG. 9 depicts an example of an operation flow and FIG. 10 illustrates a result of reading a wireless tag at certain timing during operation of the article position acquiring system 10.

In the blood collecting room, the sample is contained in advance in the sample container 200 to which the wireless tag 300 is attached. In this case, the identification number of the wireless tag 300 and a personal number for identifying the patient are linked and input to a server (not illustrated). The plurality of sample containers 200 are inserted into the support portions 22 of the sample rack 20 and conveyed to the analysis room.

In the analysis room, the external operation control device 100 is put on the sample rack 20. Here, a user inputs instructions to the input unit 52 of the information processing terminal 50 to start the position acquiring operation and starts the operation (Act01). The external operation control device 100 causes the external input value change unit 132 to operate and, for example, an external input to the input unit 340 of the wireless tag 300 attached to the sample container 200 is performed at a point (1, 1) (Act02). As described with reference to FIG. 8, the annular portion 121 is reduced in diameter to electrically connect the external input terminals 341 and 342. Therefore, the external signal is input as the ON signal to the Bank01 EPC memory 322 or the Bank11 USERmemory 324. Although the ON signal is input, it is related to the point (1, 1) as described above, so indirect position information is added.

Next, the wireless communication device 40 wirelessly and collectively reads the wireless tags 300 of all the sample containers 200 in the sample rack 20 via the antenna device 30 (Act03).

The information processing terminal 50 extracts an identification number (for example, AABBCCDDEEFF) from the reading result of the plurality of wireless tags 300 and derives a fact that the wireless tag 300 is present at the point (1, 1) at which external operation control is performed (Act04). Similarly, the article position acquiring system 10 changes the points (Act02) and repeats calculation (Act04) of the sample position information until reading of the wireless tag 300 is performed at all points (1, 1) to (m, n) (Act05). In this case, the article position acquiring system 10 integrates the number which can actually be read by the wireless tag 300 as the number of sample containers. When the sample position information calculating operation is completed at all points, the article position acquiring system 10 stops the reading of the wireless tag 300 (Act06).

The information processing terminal 50 displays the calculated position of sample containers and the number of samples on the display 53 (Act07), and completes the operation (Act08). When the user of the article position acquiring system 10 comprehends overlooking of the wireless tag 300 from the number of samples and the display result on the sample rack 20, the user can easily identify the position of the overlooked sample container 200 by comparing the display result with the sample rack 20. For only the overlooked sample container 200, the reading operation may be performed again by using a handy wireless tag reader (not illustrated) or the like. As described above, the presence or absence of the sample container 200 can be found without omission, and the position in the sample rack 20 can also be specified.

As described above, according to the article position acquiring system 10 of the embodiment, the wireless tags 300 attached to the sample containers 200 contained in the sample rack 20 are wirelessly and collectively read, and the position of the sample container 200 within the sample rack 20 and the identification number read from the wireless tag 300 can be displayed by linking therebetween. Therefore, it is possible to prevent the wireless tag 300 attached to the sample container 200 from being overlooked and loss of the sample container 200 can be found at an early stage. Thus, it is possible to improve inspection efficiency of the sample.

In the article position acquiring system 10 configured as described above, it is also possible to identify the position of the sample containers 200 by another procedure. FIG. 11 depicts an example of the operation flow, and FIGS. 12A to 12F illustrate the reading results of wireless tag at certain timing during the operation of the article position acquiring system 10.

The operation of the device is started based on an operation input received by the input unit 52 of the information processing terminal 50 (Act11). The external operation control device 100 performs, for example, the external input to the input unit 340 for each sample container 200 in a row of m=1, (Act12), and obtains a result in FIG. 12A. Subsequently, reading continues row by row until m=m continuing with a case of m=2 and a case of m=3 (Act13). When reading for each row is completed, next, reading continues column by column until n=n continuing with a case of n=1 and a case of n=2. When reading of each row and column is completed (Act14), the position of the sample container 200 is calculated from the reading result (Act15).

From the results of FIGS. 12A and 12D, it is determined that the external input is ON at the position (1, 1) and the wireless tag 300 with the identification number (for example A00000009832) is at the position (1, 1). Similarly, from the results of FIGS. 12B and 12F, it is possible to acquire that the identification number (for example, B00000004885) is positioned at a position (3, 3), and from the results of FIGS. 12C and 12E, it is possible to acquire that the identification number (for example, AABBCCDDEEFF) is positioned at a position (5, 2).

Thereafter, the reading of the wireless tag 300 is stopped (Act 16), and the information processing terminal 50 displays the calculated position of the sample container and number of samples on the screen of the display 53 (Act 17), and ends the operation (Act 18).

As described above, the way of specifying the position of the sample container 200 is such that the external input is made to the input unit 340 of the wireless tag 300 for the plurality of sample containers 200 simultaneously for each column or each row, and a method of calculating and determining may be used after all inputs are completed.

According to the article position acquiring system 10 according to the embodiment, the wireless tags 300 attached to the sample containers 200 contained in the sample rack 20 are wirelessly and collectively read, and the position of the sample container 200 within the sample rack 20 and the reading result can be displayed by linking therebetween also by the method described above. Therefore, it is possible to prevent the wireless tag 300 attached to the sample container 200 from being overlooked. Thus since loss can be detected at an early stage, it is possible to improve inspection efficiency of the sample.

Figure 13:
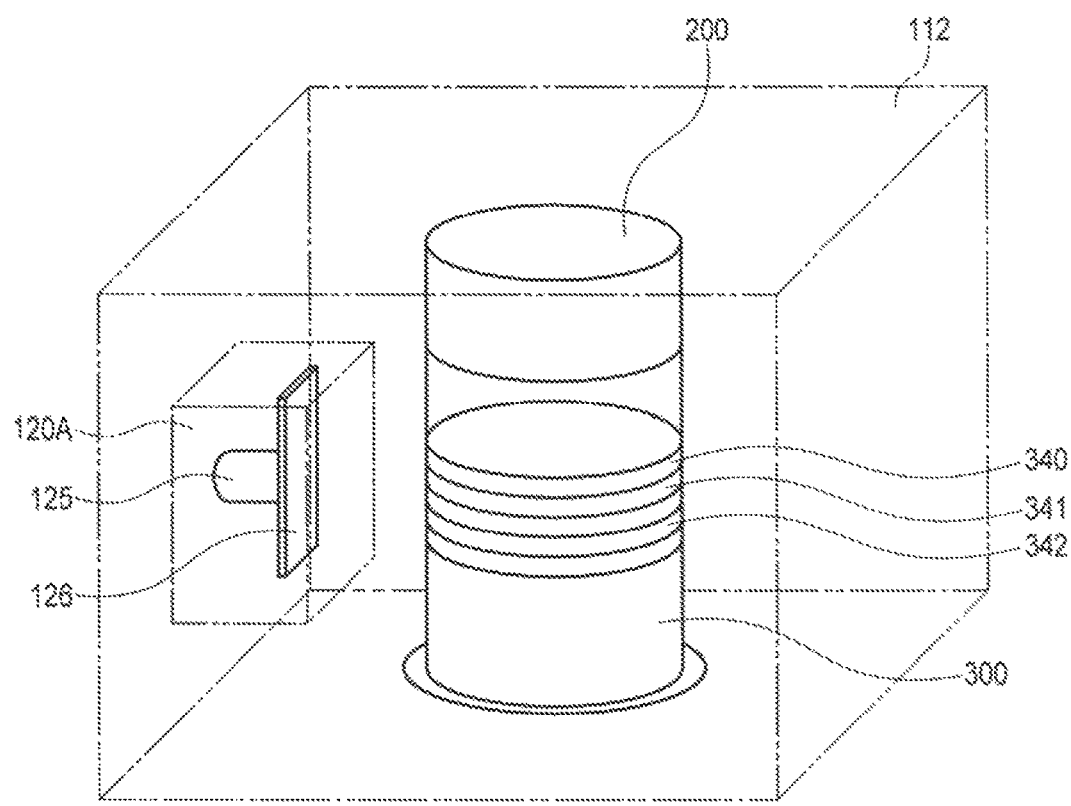
FIG. 13 is a perspective view illustrating a modification example of the external operation unit in the embodiment.

An external operation unit 120A illustrated in FIG. 13 is used if the external input terminals 341 and 342 are provided apart from each other in the axial direction of the sample container 200. That is, the external operation unit 120A includes a piston mechanism 125 provided on an inner wall surface of the recessed portion 112, and a metal plate 126 provided at a tip of the piston mechanism 125. The pair of external input terminals 341 and 342 are electrically connected by operating the piston mechanism 125 and abutting the metal plate 126 against the pair of external input terminals 341 and 342, become electrically disconnected by returning the piston mechanism 125 to an original state thereof. That is, also in the external operation unit 120A, it is possible to change the external input terminals 341 and 342 between a first state in which the external input terminals 341 and 342 are electrically connected and a second state in which the external input terminals 341 and 342 are not electrically connected.

Figure 14:
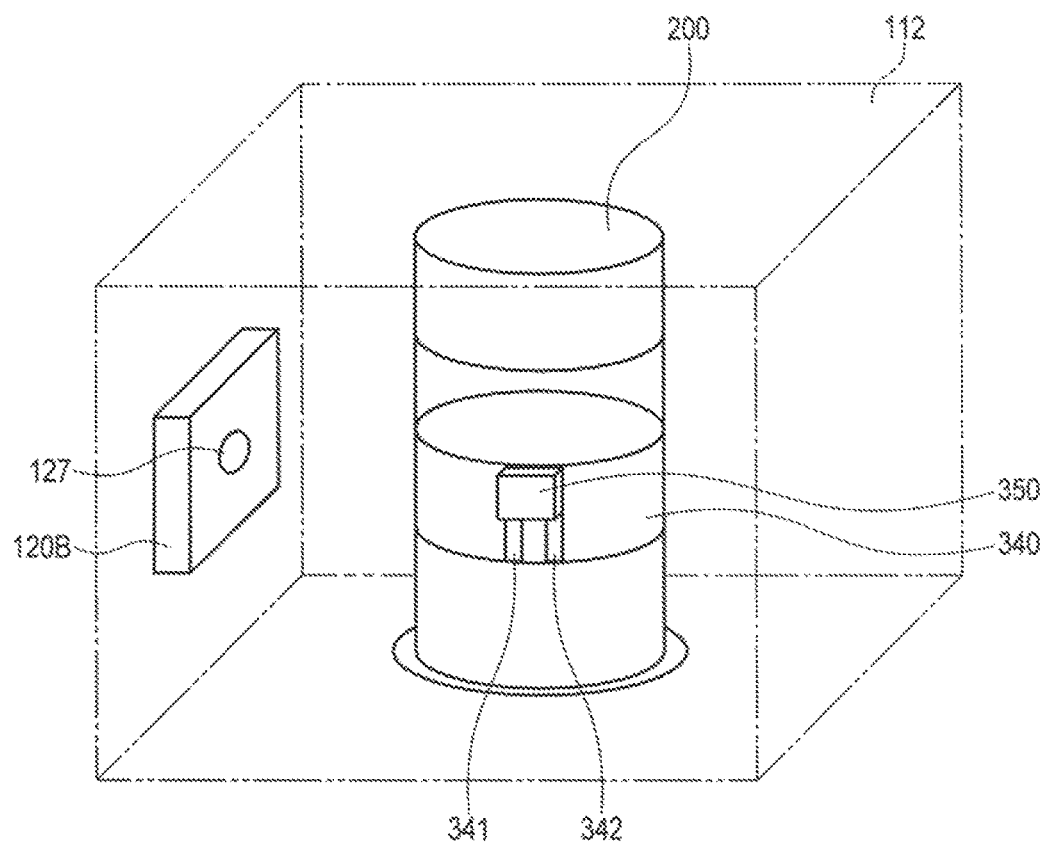
FIG. 14 is a perspective view illustrating a modification example of the external operation unit in the embodiment.

An external operation unit 120B illustrated in FIG. 14 is used if an illuminance sensor 350 is connected to the external input terminals 341 and 342. That is, a photodiode 127 is provided in the external operation unit 120B, and a received value of the illuminance sensor 350 is changed by ON/OFF of the photodiode 127. Based on the received value of the illuminance sensor 350, the flag status of the wireless tag 300 is switched. In addition to the illuminance sensor 350, it may be an electromagnetic relay, and a structure, which changes the state of the external input terminals 341 and 342 with the connection and disconnection of a magnet or ON/OFF of an electromagnet.

Figure 15:
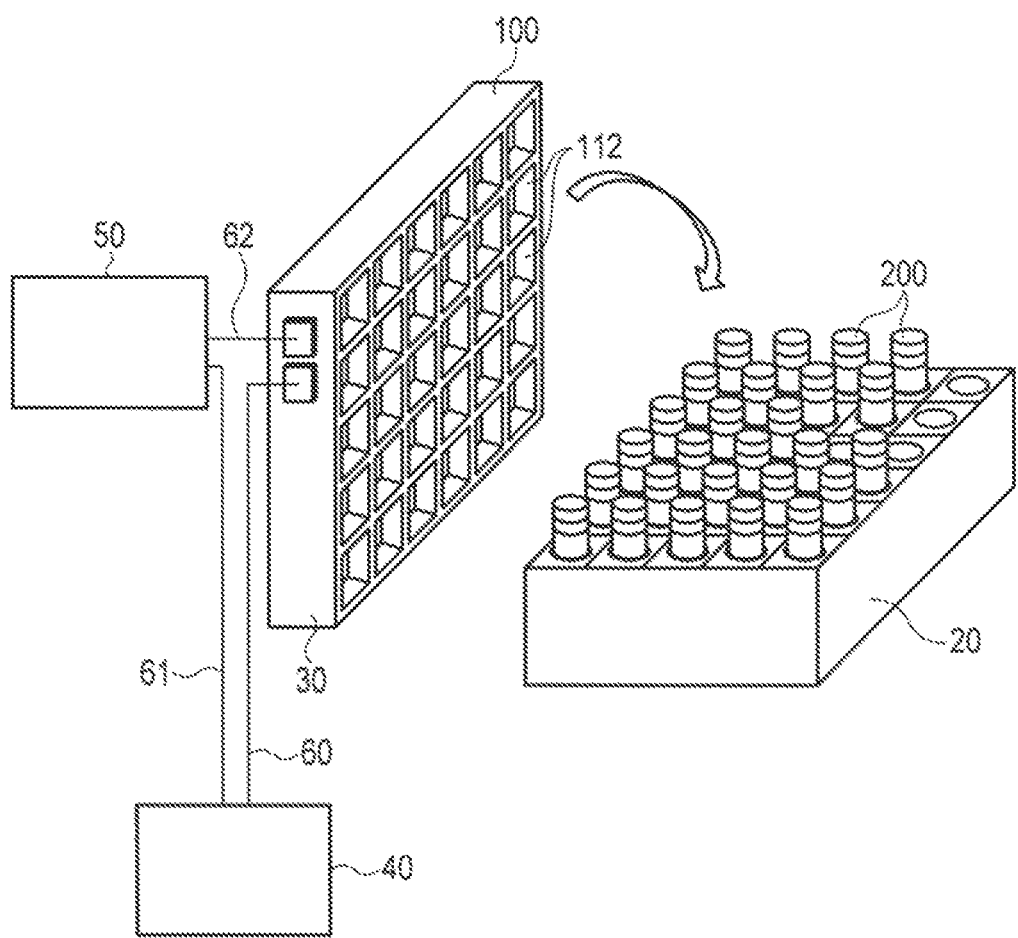
FIG. 15 is an explanatory view illustrating another configuration of the article position acquiring system according to the embodiment.

FIG. 15 illustrates another example of the configuration of the external operation control device 100, in which the wireless communication device 40, the antenna device 30, and the external operation control device 100 are integrated. Also in the article position acquiring system 10 according to the embodiment, it is possible to obtain the same effect as that of the article position acquiring system 10 illustrated in FIG. 1.

Figure 16:
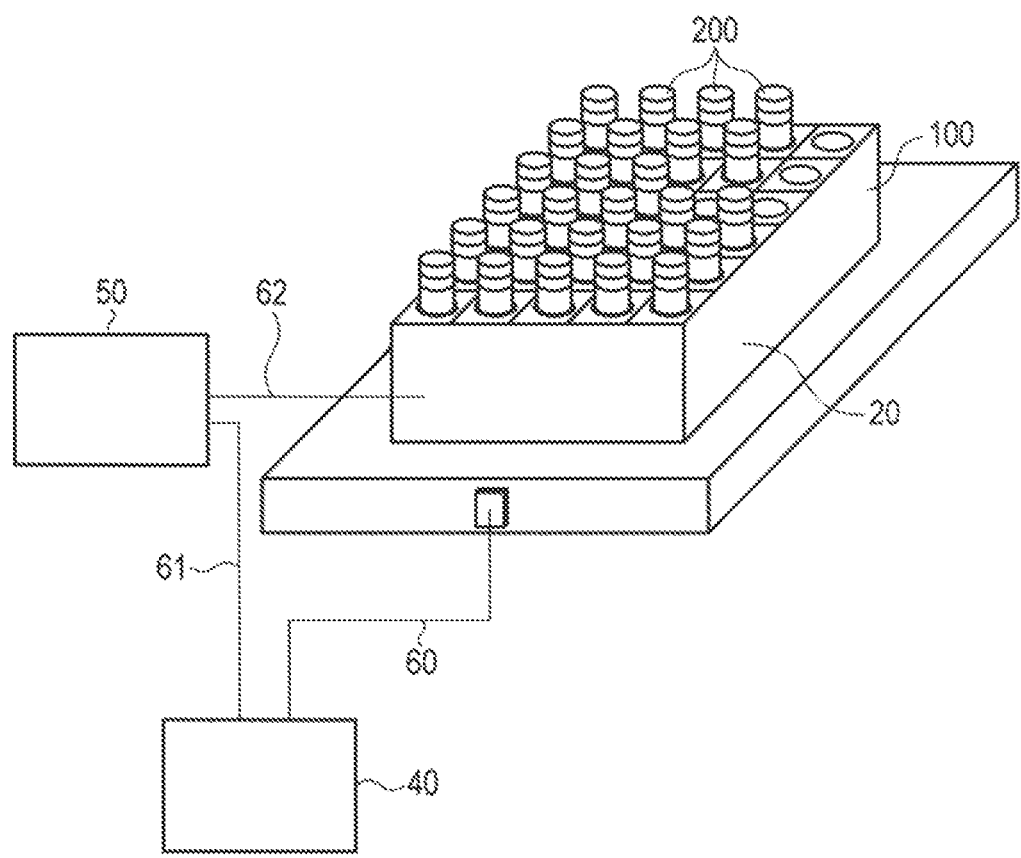
FIG. 16 is an explanatory view illustrating another configuration of the article position acquiring system according to the embodiment.

FIG. 16 illustrates another example of the configuration of the external operation control device 100, in which the external operation control device 100 and the sample rack 20 are integrated. In the configuration example, although it is necessary to transfer the sample container 200 from the sample rack 20, no operation of covering the external operation control device 100 is required, and it is possible to obtain the same effect as that of the article position acquiring system 10 illustrated in FIG. 1.

Figure 17:
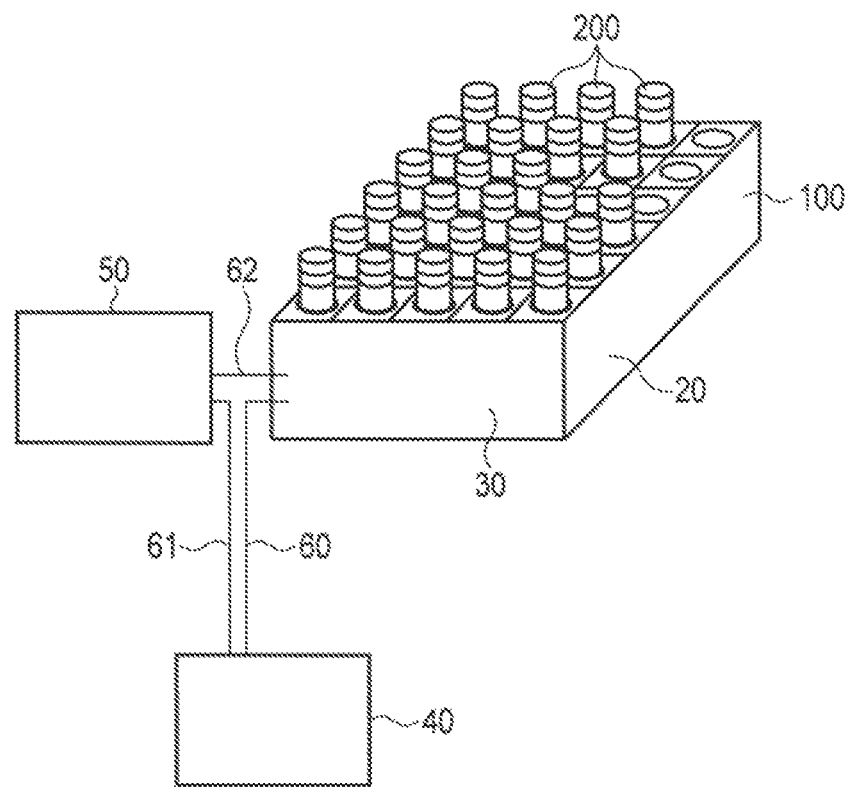
FIG. 17 is an explanatory view illustrating another configuration of the article position acquiring system according to the embodiment.

FIG. 17 illustrates another example of the configuration of the external operation control device 100, in which the antenna device 30, the sample rack 20, and the external operation control device 100 are integrated. In the configuration example, although it is necessary to transfer the sample container 200 from the sample rack 20, no operation of covering the external operation control device 100 is required, and it is possible to obtain the same effect as that of the article position acquiring system 10 illustrated in FIG. 1.

In the embodiment, the system, in which the system user performs specifying of the sample container linked with the overlooked wireless tag by comparing the display result with the position of the sample container on the rack, is provided. However, for example, a mechanism may be adopted in which a position of a sample container on a sample rack imaged by a camera or the like is linked with a result of a sample position acquiring system, and the position of the sample overlooked by image recognition is displayed on a display. In order to register the overlooked sample container in the system, it is also possible to provide a mechanism for connecting a handy antenna or the like for sample reading separately from the wireless communication device. Although the sample has been described in the exemplary embodiment, it is not limited thereto, and, for example, it may be used for management of jewelry.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A control device for wireless tags which are respectively attached to a plurality of articles supported respectively on a plurality of support portions and respectively store identification numbers of the articles, the device comprising:
   positioning portions that are respectively provided corresponding to the plurality of support portions; and
   input devices that are positioned respectively in the positioning portions, each of the input devices being configured to switch a flag status of one of the wireless tags, wherein
   the input devices are individually controllable,
   each of the wireless tags includes a pair of terminals and a flag thereof is set when the terminals become electrically connected to each other as a result of operating the corresponding input device, and
   the corresponding input device is one of a conductive annular strip which is wrapped around the terminals and tightened to cause the terminals to become electrically connected to each other or a conductive plate which is moved to contact the terminals to cause the terminals to become electrically connected to each other.

2. The device according to claim 1, wherein the support portions include a first support portion and the positioning portions include a first positioning portion corresponding to the first support portion, and the input device positioned in the first positioning portion is controlled to switch the flag status of a first wireless tag attached to a first article that is supported by the first support portion.

3. The device according to claim 1, wherein each of the wireless tags includes a sensor, and a flag thereof is set when the sensor detects an activation signal from the corresponding input device.

4. The device according to claim 3, wherein the sensor is an illumination sensor and the corresponding input device is a photodiode, which is turned on to set the flag of the wireless tag.

5. The device according to claim 3, wherein the sensor is an electromagnetic relay and the corresponding input device is an electromagnet, which is turned on to set the flag of the wireless tag.

6. An article position acquiring system, comprising:
   a plurality of support portions on which articles having wireless tags are to be supported;
   positioning portions that are respectively provided corresponding to the plurality of support portions;
   input devices that are positioned respectively in the positioning portions each of the input devices being configured to switch a flag status of one of the wireless tags;
   a control device configured to control the input devices one by one; and
   a wireless communication device configured to acquire position information from the control device and article information and the flag status from the wireless tags, wherein
   each of the wireless tags includes a pair of terminals and a flag thereof is set when the terminals become electrically connected to each other as a result of operating the corresponding input device,
   the corresponding input device is one of a conductive annular strip which is wrapped around the terminals and tightened to cause the terminals to become electrically connected to each other or a conductive plate which is moved to contact the terminals to cause the terminals to become electrically connected to each other.

7. The system according to claim 6, wherein the support portions include a first support portion and the positioning portions include a first positioning portion corresponding to the first support portion, and the control device controls the input device positioned in the first positioning portion to switch the flag status of a first wireless tag attached to a first article that is supported by the first support portion.

8. The system according to claim 6, wherein each of the wireless tags includes a sensor, and a flag thereof is set when the sensor detects an activation signal from the corresponding input device.

9. The system according to claim 8, wherein the sensor is an illumination sensor and the corresponding input device is a photodiode, which is turned on to set the flag of the wireless tag.

10. The system according to claim 8, wherein the sensor is an electromagnetic relay and the corresponding input device is an electromagnet, which is turned on to set the flag of the wireless tag.

11. An article position acquiring method for acquiring a position of each of a plurality of articles using wireless tags which are respectively attached to the articles and respectively store identification numbers of the articles, the method comprising:
   supporting the articles respectively on support portions, wherein each of the support portions has a corresponding positioning portion in which an input device is disposed;

controlling the input devices one by one for electrically connecting a pair of terminals of each of the wireless tags to each other to switch a flag status of the corresponding wireless tags one by one, each of the input devices being one of a conductive annular strip which is configured to be wrapped around the terminals and tightened or a conductive plate which is configured to be moved to contact the terminals;

acquiring identification information and the flag status from each of the wireless tags; and acquiring position information of each of the input devices as they are controlled one by one.

12. The method of claim 11, wherein the support portions are arranged in a rectangular grid and the position information specifies row and column of the rectangular grid.

13. The method of claim 11, wherein each of the wireless tags includes a sensor and a flag thereof is set when the sensor detects an activation signal from the corresponding input device.

\* \* \* \* \*